United States Patent
Both et al.

(10) Patent No.: US 8,857,263 B2
(45) Date of Patent: Oct. 14, 2014

(54) ULTRASONIC PROBE AND METHOD FOR THE NONDESTRUCTIVE TESTING OF A PLANAR TEST SPECIMEN

(75) Inventors: Norbert Both, Tholey (DE); Frank Niese, Saarbrücken (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 386 days.

(21) Appl. No.: 13/457,530

(22) Filed: Apr. 27, 2012

(65) Prior Publication Data

US 2012/0272739 A1  Nov. 1, 2012

(30) Foreign Application Priority Data

Apr. 29, 2011 (DE) .......................... 10 2011 018 954

(51) Int. Cl.
| | |
|---|---|
| G01N 29/00 | (2006.01) |
| G01N 29/26 | (2006.01) |
| G01N 29/22 | (2006.01) |
| G01N 29/04 | (2006.01) |

(52) U.S. Cl.
CPC ............ *G01N 29/041* (2013.01); *G01N 29/262* (2013.01); *G01N 2291/263* (2013.01); *G01N 2291/106* (2013.01); *G01N 29/26* (2013.01); *G01N 29/221* (2013.01)
USPC ............................................. 73/632; 73/622

(58) Field of Classification Search
USPC .......................................... 73/632, 622, 627
See application file for complete search history.

(56) References Cited

U.S. PATENT DOCUMENTS

| | | | | |
|---|---|---|---|---|
| 7,698,944 B2* | 4/2010 | Takada | ............................ | 73/588 |
| 7,819,010 B2 | 10/2010 | Alers et al. | | |
| 7,994,689 B2* | 8/2011 | Sawada et al. | ................ | 310/334 |
| 8,024,975 B2* | 9/2011 | Yabushita et al. | ............... | 73/628 |
| 8,037,764 B2 | 10/2011 | Kröning et al. | | |
| 8,181,524 B2* | 5/2012 | Hara et al. | ....................... | 73/587 |
| 8,225,668 B2* | 7/2012 | Yabushita et al. | .............. | 73/624 |
| 2008/0289425 A1 | 11/2008 | Dijkstra et al. | | |

FOREIGN PATENT DOCUMENTS

| | | |
|---|---|---|
| DE | 42 04 643 C1 | 5/1993 |
| DE | 10 2004 053 584 A1 | 11/2004 |
| DE | 10 2004 063 482 B3 | 12/2004 |
| DE | 10 2008 002 394 A1 | 10/2009 |
| EP | 0 556 557 B1 | 8/1993 |

OTHER PUBLICATIONS

Wilcox, P. et al: "Lamb and SH Wave Transducer Arrays for the Inspection of Large Areas of Thick Plates, in Review of Progress in QNDE 2000", 19, pp. 1049-1056.

* cited by examiner

*Primary Examiner* — J M Saint Surin
(74) *Attorney, Agent, or Firm* — Antonelli, Terry, Stout & Kraus, LLP.

(57) ABSTRACT

An ultrasonic probe and a method for the nondestructive testing of a test specimen are described, which are activatable individually or in groups as phased array for the emission or reception of ultrasonic plate waves in a predefinable propagation direction in the test specimen wall to be tested. At least one ultrasonic transducer segment with at least two segment parts emits an ultrasonic plate wave field into the test specimen and which are activatable jointly and simultaneously as a phased array. The at least two segment parts are arranged along a common plane so that the ultrasonic wave fields provided from or received by the at least two segments mutually overlap and each have a main propagation direction which encloses an acute angle α in a projection of the plane.

36 Claims, 3 Drawing Sheets

Figure 1:
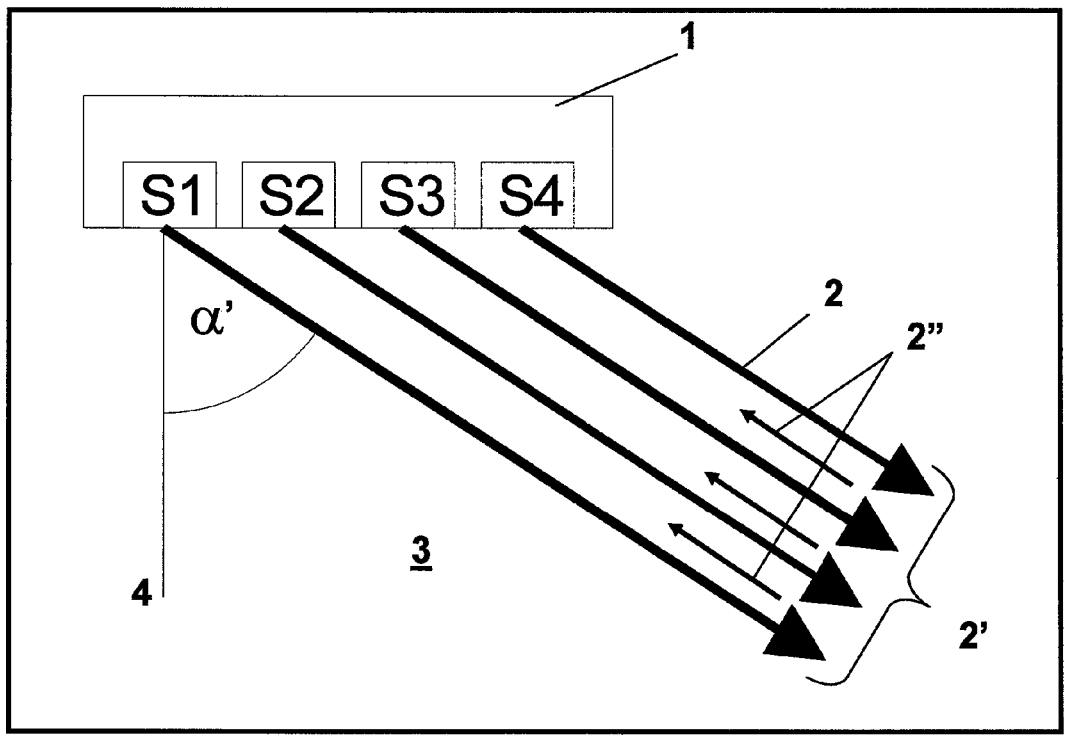
Figure 1:
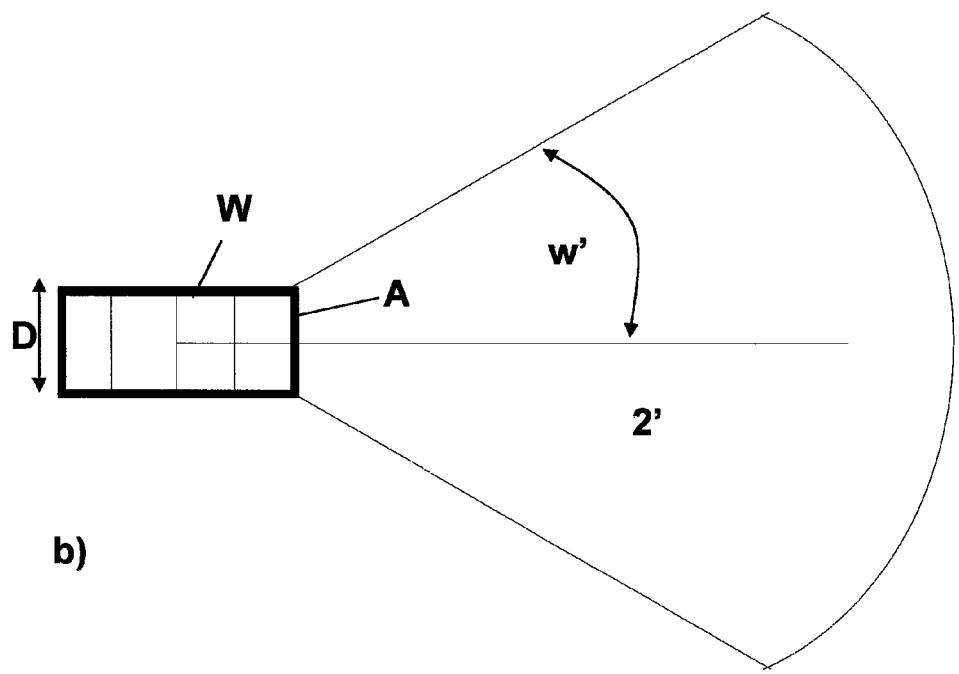

ULTRASONIC PROBE AND METHOD FOR THE NONDESTRUCTIVE TESTING OF A PLANAR TEST SPECIMEN

CROSS REFERENCE TO RELATED APPLICATION

Reference is made to German Patent Application Serial No. 10 2011 018 954.8, entitled "Ultrasonic Probe and Method for the Nondestructive Testing of a Planar Test Specimen," filed Apr. 29, 2011, which application is incorporated herein by reference in its entirety.

BACKGROUND OF THE INVENTION

1. Field of the Invention

The invention relates to an ultrasonic probe and a method for the nondestructive testing of a planar test specimen, such as a pipe wall, a slab, or a plate, which provides a plurality of ultrasonic transducer segments, which are activatable individually or in groups by means of phased array technology for the emission of ultrasonic plate waves having a predefinable propagation direction in the test specimen to be tested.

2. Description of the Prior Art

Ultrasonic probes of the above-mentioned species are used, for example, in the nondestructive testing of extended test objects, in order to detect cracks or other types of material defects in test specimens or test specimen walls. In particular in the examination of weld seams, the ultrasonic waves are incident at an inclined angle relative to the weld seam as much as possible, in order to detect weld seam defects either in a reflection, diffraction, or transmission measurement in this manner.

In addition to the incidence of the ultrasonic signals in a test specimen wall to be studied at a permanently predefined incidence angle, due to which it is necessary to move the ultrasonic probe used for this purpose relative to the weld seam to register the entire weld seam geometry, ultrasonic probes are known and are in use which, based on the phased array technology, allow a variation of the incidence angle of the ultrasonic waves during the testing. Using this electronic pivoting technique, during which the main propagation direction of the ultrasonic wave field which can be coupled into the test specimen is pivoted, probe movements in the direction of the weld seam can be omitted or minimized, whereby nondestructive ultrasonic examinations on test specimens can be performed more rapidly and therefore more cost-effectively.

Ultrasonic probes, which are also referred to as phased array probes, which are suitable for the use of the phased array technology, consist of a plurality of individually activatable ultrasonic transducer segments, which generate ultrasonic waves. The individual segments, which generate ultrasonic waves are combined to form a phased array probe, are differently activated in the case of transmission or differently read out in the case of reception. In most cases, the differing activation of the individual segments is performed by individual amplitude and/or phase configuration or by a time-delayed activation, in order to achieve an angular incidence or focusing of the ultrasonic wave field, which results through superposition of the individual fields originating from the ultrasonic transducer segments and which is emitted as a whole by the phased array probe.

In spatially delimited test specimens to be studied, for example, plates or plate-shaped test specimens, so-called ultrasonic plate waves can form, whose propagation direction is oriented parallel to the plate surface and whose ultrasonic wavelength is of the magnitude of the plate thickness. In addition to classical piezoelectric angle probes, electromagnetic ultrasonic transducers can also be used for the excitation and reception of such ultrasonic plate waves, during which a selective excitation of selected plate wave modes and also plate waves having an SH polarization are possible. The latter relates to shear waves, which are polarized parallel to the wall surface. Therefore, these waves can also be referred to as "horizontally polarized shear waves" or, for the case of plate waves, as "horizontally polarized plate waves".

In order to set a specific incidence direction in a voluminously extended test specimen, the known phased array technology can be used. Segmented ultrasonic probes are used, which can be activated in a phase-oriented manner using suitable electronics. This approach can also be used for the excitation of ultrasonic plate wave modes. It is thus possible, if the emission direction of the segments is aligned perpendicularly to the linear arrangement of the segments, to rotate the emission direction of the ultrasonic summation signal through a phase-oriented activation in the plate plane. See P. Wilcox, M. Lowe, and P. Cawley: Lamb and SH Wave Transducer Arrays for the Inspection of Large Areas of Thick Plates, in Review of Progress in QNDE 2000, 19, pages 1049-1056. However, it is problematic that the pivot range of the ultrasonic wave field is limited by the aperture width of each individual ultrasonic transducer segment.

The publication DE 10 2004 063 482 B3 describes an arrangement for the incidence of US shear waves into a tubular or slab-shaped ferromagnetic test specimen for the crack testing thereof. Both the emission and also the reception of the US shear waves are performed with the aid of an HF coil arrangement, which is attached to a probe, which is pre-magnetized in the area of the HF coil arrangement.

DE 10 2004 053 584 A1 discloses nondestructive material testing utilizing of ultrasound, in which EMUS transducers are used to generate ultrasonic waves which can be emitted into the test specimen perpendicular to the test specimen surface.

Finally, DE 10 2008 002 394 A1 describes a universal ultrasonic probe for the emission of ultrasonic waves which propagate within a test specimen parallel to the test specimen surface, predominantly for studying welding melt zones. The probe is ring-shaped and has segmented separate regions for the emission and the reception of ultrasonic waves.

SUMMARY OF THE INVENTION

The invention is a refinement of an ultrasonic probe for the nondestructive testing of a planar test specimen, such as a pipe wall, a slab, or a plate, having an ultrasonic probe. The probe has a plurality of ultrasonic transducer segments, which are activatable individually or in groups in a phased array at least for the emission of ultrasonic plate waves having a predefinable propagation direction in the test specimen to be tested. The pivot range, within which the ultrasonic plate waves can be generated having predefinable propagation direction, is enlarged. The enlargement of the pivot range is to be implementable using the simplest possible technical means, which are cost-effective to implement.

A method according to the invention for the nondestructive testing of a planar test specimen, such as a pipe wall, a slab, or a plate, is described. Features which advantageously refine the invention are the subject matter of the further description, in particular with reference to the exemplary embodiments.

According to the invention, an ultrasonic probe for the nondestructive testing of a planar test specimen, such as a pipe wall, a slab, or a plate, includes a plurality of ultrasonic transducer segments, which are activatable individually or in groups by means of a phased array at least for the emission of ultrasonic plate waves having a predefinable propagation direction in the test specimen to be tested. The at least one ultrasonic transducer segment has at least two segment parts, from each of which an ultrasonic plate wave field can be emitted into the planar test specimen and which are activatable jointly, that is, simultaneously, by as a phased array. The at least two segment parts are arranged along a common plane so that the ultrasonic wave fields assignable to the at least two segments mutually overlap and each have a main propagation direction, which enclose an acute angle α in a projection on the plane.

The invention differs from the previous implementation of individual ultrasonic transducer segments in that the ultrasonic transducer segments, which are each implemented as a unit, are split into at least two halves which are separated into at least two spatially separated units, each of which generate or originate an ultrasonic wave field. Both halves of an ultrasonic transducer segment, that is, both segment parts, are disposed in a common plane and enclose an acute angle relative to one another, so that the ultrasonic plate wave fields originating from both segment parts each have a main propagation direction. The main propagation directions enclose an acute angle relative to one another. The ultrasonic plate wave fields generated by both segment parts are superimposed to form an ultrasonic plate wave field having a divergence angle, which is greater than a divergence angle or aperture angle of an ultrasonic wave field which originated from a non-divided, prior art ultrasonic transducer segment.

Through the measure according to the invention of the division of an ultrasonic transducer segment into at least two parts, which are not arranged in parallel but rather at an acute angle to one another, the pivot range of the phased array ultrasonic probe for emitting ultrasonic plate waves can be enlarged, to expand the spectrum of application of ultrasonic probes.

The invention is applicable to piezoelectric and also electromagnetic ultrasonic transducers. A division of the prior art ultrasonic transducer segment into two parts to implement the invention is also not limiting. The emission divergence of an ultrasonic transducer segment may be enlarged further by the ultrasonic transducer segment being divided into three, four, or more segment parts, which preferably have an identical structural design and in which each two adjacent segment parts are disposed in a plane enclosing an acute angle α. The angle α fundamentally may be varied so that 0°<α<0°, but preferably α is <60°, particularly preferably α is less <15°.

A preferred embodiment divides the ultrasonic transducer segment into two segment parts of equal size, that is, into a segment part pair, which jointly enclose the acute angle α according to the invention.

A preferred embodiment of an ultrasonic probe according to the invention provides a line-shaped arrangement of a plurality of segment part pairs, whose assignable transmission and/or reception apertures face toward the same half space. The individual segment part pairs are preferably activated in the same manner as the prior art individual phased arrays so that both halves of a segment part pair are activated simultaneously, that is, at the same time. In contrast respective adjacently arranged segment part pairs are activated, for example, with a phase delay or time delay based on the prior art phased array. As a result, a total ultrasonic plate wave field is emitted by the ultrasonic probe implemented according to the invention, that is., by the sum of all segment part pairs arranged adjacent to one another, providing a superposition field composed of all individual wave fields of the segment part pairs which propagates at a predefinable emission angle or based on a predefinable focal area.

Depending on the arrangement and implementation of the ultrasonic probe, ultrasonic plate wave fields can be both generated or received according to the invention.

The method of operation on the device according to the invention is distinguished by at least two separate ultrasonic transducer fields, which come into spatial superposition with one another, being emitted and/or received by at least one ultrasonic transducer segment. A main propagation direction is assignable to each segment, which encloses an acute angle α relative to one another.

The above-described at least one transducer segment is to be understood according to the invention as the "occurrence location" for the formation or occurrence of at least two separate ultrasonic wave fields, which are spatially superposed with one another. The method according to the invention can be physically implemented in an ultrasonic transducer segment which is formed in one, two, or multiple parts. It is essential that, from the location of an ultrasonic transducer segment within a plurality of arranged ultrasonic transducer segments, from which an ultrasonic plate wave field having predefinable propagation direction can be generated based on prior art phased arrays. At least two separate ultrasonic plate wave fields originate, which come into spatial superposition, each having an assignable main propagation direction, which in turn encloses an acute angle α relative to one another. To implement this requirement using the simplest possible technical means, the above separation of an ultrasonic transducer segment into at least two halves is utilized. Alternative measures, which are more technically complex to implement, however, are also applicable.

With the method according to the invention, the emission divergence of the ultrasonic plate wave fields emitted from each "occurrence location" is enlarged in comparison to the prior art implementation of ultrasonic phased array probes. In particular, the emission divergence of the overall ultrasonic plate wave field emitted from all "occurrence locations" is also enlarged. In this way the pivot range, within which the main propagation direction of the total ultrasonic plate wave field can be varied, can also be enlarged according to the invention.

BRIEF DESCRIPTION OF THE INVENTION

Figure 2:
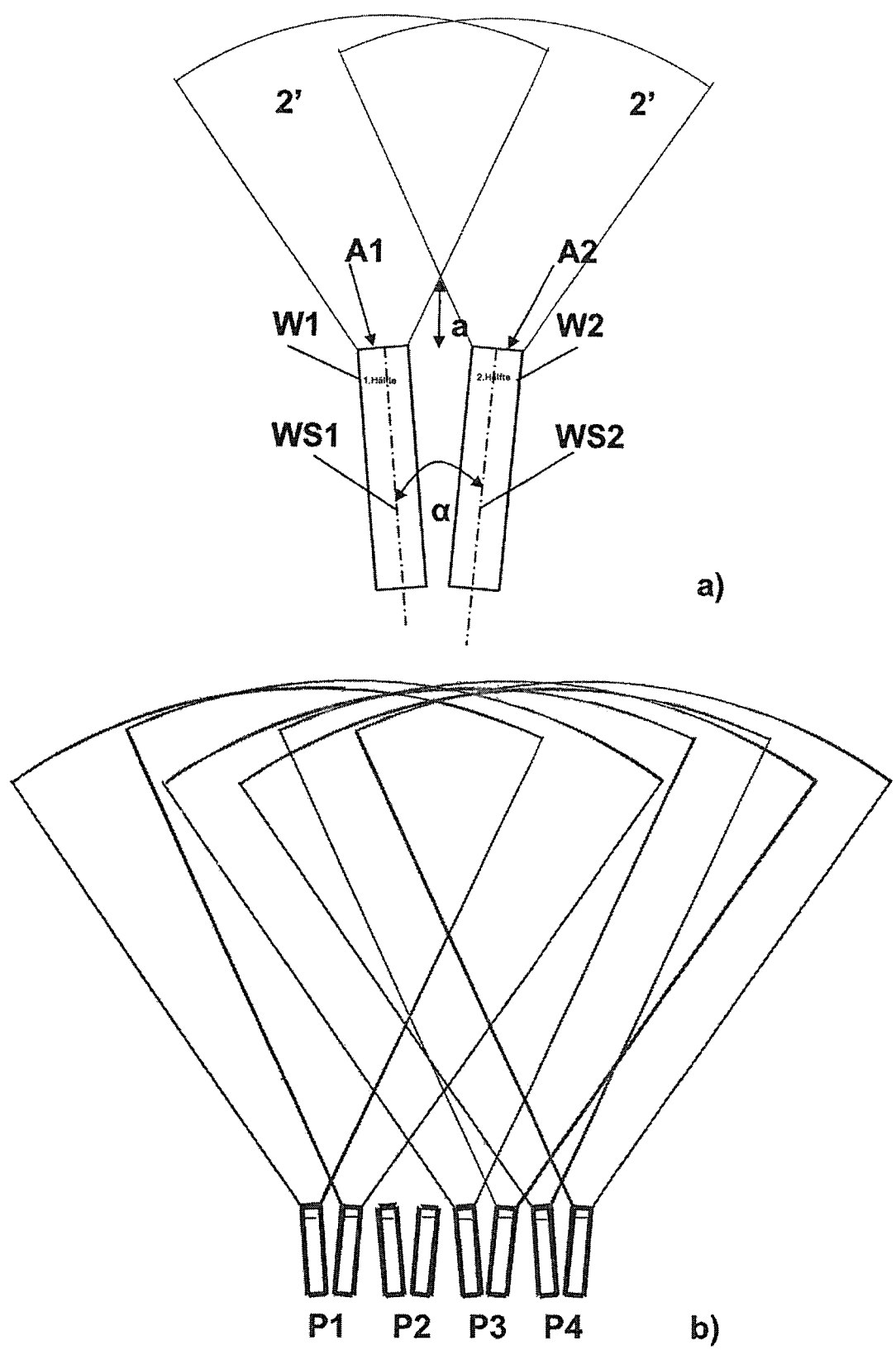
Figure 3:
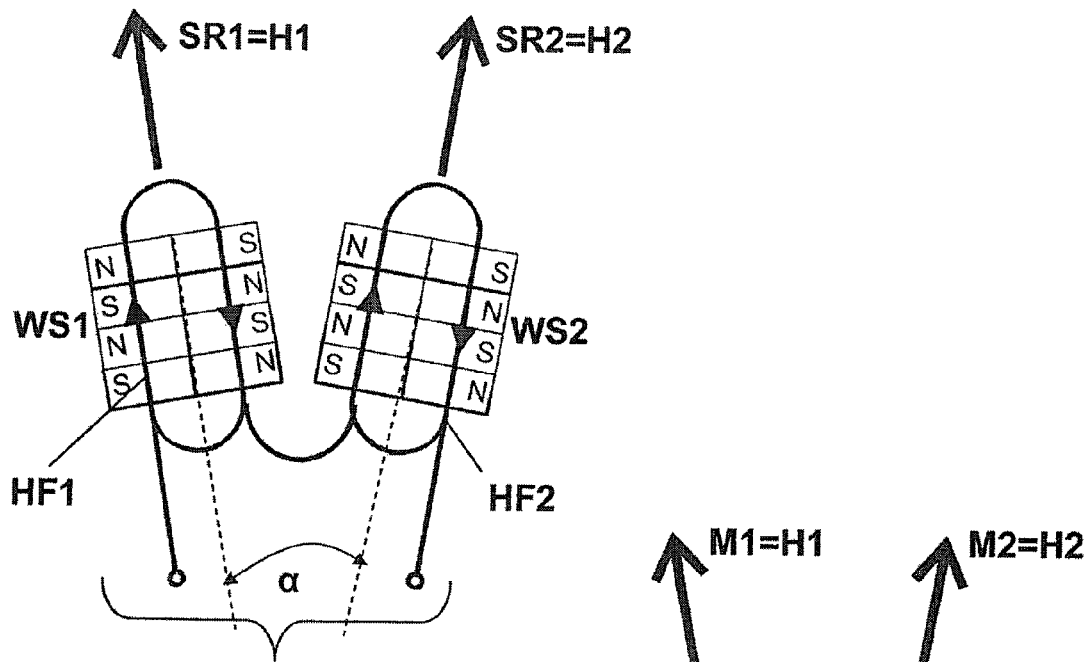
Figure 4:
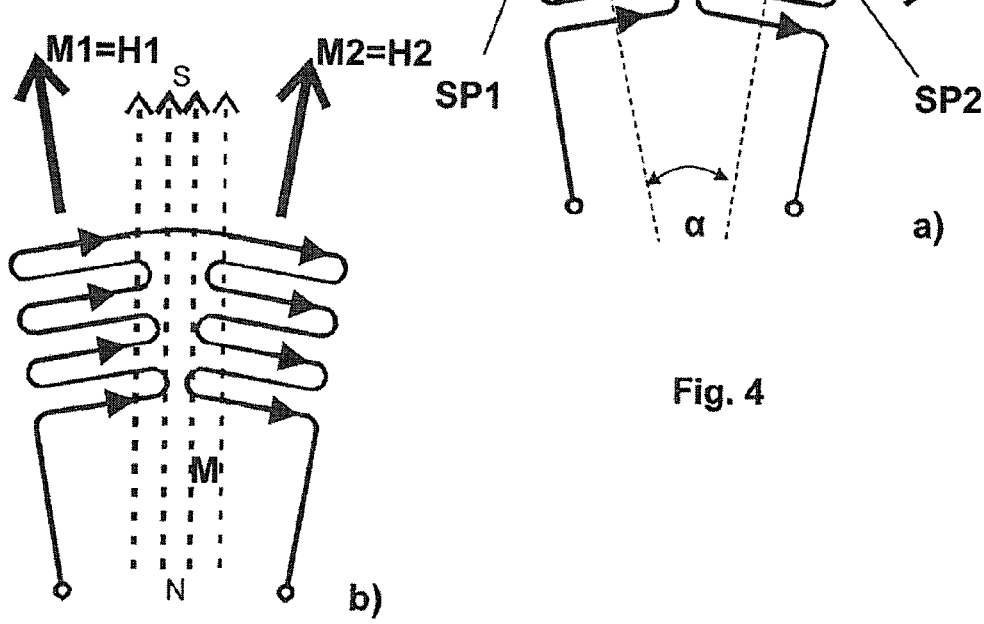

The invention will be described for exemplary purposes hereafter without restriction of the invention on the basis of exemplary embodiments with reference to the drawings. In the figures:

FIGS. 1a and b show an illustration of a prior art ultrasonic probe, which is known per se, for generating ultrasonic plate waves and a view of an ultrasonic transducer segment;

FIGS. 2a and b show an arrangement according to the invention of two segment part pairs or a plurality of segment pairs;

FIG. 3 shows an embodiment of a segment part pair based on an electromagnetic ultrasonic transducer; and FIGS. 4a and b show an alternative embodiment of a segment part pair of the invention based on an electromagnetic ultrasonic transducer.

DESCRIPTION OF THE INVENTION

FIG. 1a shows a schematic view to illustrate a prior art ultrasonic probe 1 known per se, which has four ultrasonic transducer segments S1, S2, S3, and S4. The four ultrasonic transducer segments S1 to S4 are implemented to generate ultrasonic plate waves 2, which are capable of propagating in the exemplary embodiment shown within a test specimen wall 3, which is coincident with the plane of the drawing of FIG. 1a.

The individual ultrasonic transducer segments S1 to S4 are activated with a phase delay or time delay in a suitable manner by means of phased array technology, in order to obtain an ultrasonic plate wave field 2' having a main propagation direction which is pivoted through pivot angle α' relative to the uninfluenced propagation direction 4 of the individual ultrasonic transducer segments S1 to S4.

Each of the individual ultrasonic transducer segments S1 to S4 visible in FIG. 1a has a transducer body W, shown in FIG. 1b. A frontal outlet/reception aperture A has an aperture width D, which typically corresponds to the transducer width. The ultrasonic transducer segment W can be implemented both in the form of a piezo transducer or as an electromagnetic ultrasonic transducer (EMUS transducer). An ultrasonic plate wave field 2', which has an aperture angle w', which predefines the emission divergence of the ultrasonic transducer segment W, is emitted or generated within a test specimen wall frontally via the outlet aperture A. Ultrasonic plate waves 2" which are generated within the test specimen for example by reflection are detected by the ultrasonic transducer segments S1 to S4. Reflections of ultrasonic waves inside a test specimen take place at locations of discontinuities, like cracks, inhomogeneity of material, test specimen walls etc.

The emission divergence w' of the ultrasonic transducer segment W is bounded, inter alia, by the ultrasonic wave frequency and the aperture width D. At the same time, the maximum possible pivot range of an ultrasonic probe composed of a plurality of ultrasonic transducer segments, which are operated as a phased array, is also predefined by the delimitation of the divergence range. In order to widen the pivot range of the phased array ultrasonic plate wave probe and therefore make it accessible for a broader application spectrum, according to the invention the ultrasonic transducer segment implemented as a unified component shown in FIG. 1b is split into at least two halves. The halves are not arranged in parallel to form an acute angle relative to one another. This is illustrated schematically in FIG. 2a, which shows two segment parts W1 and W2 of an ultrasonic transducer segment, which are implemented structurally identical to one another and enclose an acute angle α defined by their segment longitudinal extensions WS1 and WS2. The two segment parts W1 and W2 each have an outlet aperture A1 and A2, which respectively correspond in sum to the outlet aperture of an undivided ultrasonic transducer segment according to FIG. 1b. Both segment parts W1 and W2 are arranged located adjacent to one another in a common plane, which corresponds to the plane of the drawing in FIG. 2a, and enclose with their respective segment longitudinal extensions WS1 and WS2 the acute angle α, which fundamentally varies in an angle ranging between 0° and 90°. However, the angle preferably ranges so that α<60°, particularly preferably <15°. The selection of the angle α is particularly performed in such a manner that the ultrasonic plate wave fields 2', which are emitted from both segment parts W1 and W2, mutually overlap, so that the superposition of both wave fields occurs at a minimum distance a from the outlet apertures A1 and A2.

Through the embodiment according to the invention of the at least two segment parts W1 and W2, the divergence range of the total ultrasonic plate wave field of overlapping segment parts W1 and W2, is also enlarged in comparison to a single prior art ultrasonic transducer segment according to FIG. 1b, which is known per se. The maximum pivot range of an ultrasonic probe having a plurality of divided ultrasonic transducer segments is also enlarged at the same time. This is schematically shown in FIG. 2b. FIG. 2b shows four segment part pairs P1, P2, P3, P4, which each correspond to one ultrasonic transducer segment S1, S2, S3, S4 in the ultrasonic probe 1 shown in FIG. 1. The four segment part pairs P1 to P4 shown in FIG. 2b each have two segment parts W1 and W2 arranged tilted relative to one another according to the view illustrated in FIG. 2a, and generate a total ultrasonic plate wave field from superposition of all individual ultrasonic plate wave fields. The total divergence of the four segment part pairs P1 to P4 is greater than that which is generated by the four ultrasonic transducer segments S1 to S4, so that the total pivot range, which is settable using phased arrays, can also be enlarged.

The segment part pairs P1 to P4 which are shown in FIG. 2b are arranged directly adjacent to one another in a common plane, which corresponds to the plane of the drawing in FIG. 2b with outlet apertures being located in a common plane.

The above explanations, which are referred to as ultrasonic transducer segments, are only capable of emitting ultrasonic plate wave fields. Of course, the individual segment part pairs P1 to P4 can also be used at the same time or alternatively only exclusively for receiving ultrasonic plate wave fields.

As already described, the two segment parts W1 and W2 according to FIG. 2a may be either implemented as piezo transducers or as electromagnetic ultrasonic transducers. An embodiment of two segment parts WS1 and WS2 based on an electromagnetic ultrasonic transducer principle is explained with reference to FIG. 3. Each individual segment part WS1 and WS2 has a permanent magnet array, which includes a plurality of individual bar magnets joined directly to one another in a stack. Each bar magnet has alternating magnetic poles in the stack direction SR1 and SR2. Both segment parts WS1 and WS2 are arranged to be tilted relative to one another with respect to their two stack directions SR1 and SR2 and enclose the acute angle α. In addition, each segment part WS1 and WS2 includes an HF coil including HF1 and HF2, which are both connected in series and are therefore activatable uniformly, that is, simultaneously, to generate or receive ultrasonic plate waves. Through the mutually tilted arrangement of both permanent magnet arrays, the main emission directions H1 and H2 of both segment parts WS1 and WS2, along which the ultrasonic plate waves are emitted, enclose the angle α, which enlarges the emission divergence of the illustrated segment part pair P.

A further exemplary embodiment of the implementation of an electromagnetic ultrasonic transducer is illustrated in FIG. 4a. In this case, each segment part comprises a meandering HF coil system SP1 and SP2 including a plurality of coil loops SP1 and SP2 arranged along a meandering direction M1 and M2. The meandering directions M1 and M2 enclose the acute angle α. Both meandering coils SP1 and SP2 are also connected in series and are therefore activatable simultaneously.

In addition, a permanent magnet generates a stationary or quasi-stationary magnetic field M which is oriented parallel to the surface of a test specimen wall at the location or in the region of the meandering HF coil arrangements SP1 and SP2. In the case of the exemplary embodiment illustrated in FIG. 4a, the magnetic field lines of the permanent magnetic field M are oriented substantially perpendicular to M1 and M2, and enclose an angle of 90°±α/2 relative to the meandering directions M1 and M2.

In contrast thereto, the permanent magnet field M in the exemplary embodiment according to FIG. 4b, which also has two meandering HF coil arrangements SP1 and SP2 connected in series, is aligned substantially parallel to the meandering directions M1 and M2. In particular, the magnetic field lines enclose an angle of ±α/2 relative to the meandering directions M1 and M2. Through such an arrangement, Lamb wave modes are preferably excited in the test specimen wall, while in contrast the exemplary embodiment according to FIG. 4a preferably generates SH wave modes.

LIST OF REFERENCE NUMERALS 1 ultrasonic probe
2 ultrasonic plate waves
2' ultrasonic plate wave field
3 test specimen wall
4 original propagation direction
WS1 and WS2 segment part
W ultrasonic transducer segment
D aperture width, transducer width
A aperture
w' aperture angle, divergence
SP1 and SP2 meandering HF coil arrangement
M1 and M2 meandering direction
H1 and H2 main sound emission direction
SR1 and SR2 stack direction
P1, . . . , P4 segment part pair
P segment part pair

The invention claimed is:

1. An ultrasonic probe for nondestructive testing of a test specimen, comprising:
a plurality of ultrasonic transducer segments which are activatable individually or in groups as a phased array to provide emission of ultrasonic plate waves having a predefinable propagation direction in the test specimen to be tested; and wherein:
at least one ultrasonic transducer segment includes at least two segment parts, each emitting an ultrasonic plate wave field into the test specimen and which are activatable jointly and simultaneously as a phased array and the at least two segment parts are disposed along a common plane so that the ultrasonic wave fields emitted from the at least two segments mutually overlap and each have a main propagation direction intersecting in an acute angle defined in the plane.

2. The ultrasonic probe according to claim 1, wherein:
the at least two segment parts are structurally identical and each have a longitudinal extension, are disposed adjacent to one another and are spatially separated in the plane so that the longitudinal extension of the respective two segment parts intersect to define the acute angle.

3. The ultrasonic probe according to claim 2, wherein:
the ultrasonic transducer segments emit ultrasonic plate waves.

4. The ultrasonic probe according to claim 3, wherein:
the ultrasonic transducer segments comprise a piezoelectric material for transducing sound; and
the at least two segment parts include a transducer body comprising the piezoelectric material, having a longitudinal extension, for application to the test specimen and the longitudinal extension of the transducer intersect to define the acute angle.

5. The ultrasonic probe according to claim 4, wherein:
the ultrasonic transducer segments comprise electromagnetic ultrasonic transducers and the test specimen contains at least components of ferromagnetic and/or electrically conductive material.

6. The ultrasonic probe according to claim 4, wherein:
the at least two segment parts each comprise a permanent magnet arrangement including individual bar magnets joined directly to one another in a stack with each bar magnet having magnetic poles alternating in a direction of stacking; and further comprising:
a HF coil containing coils connected in series which are each associated with a different permanent magnet arrangement and a direction of stacking of the permanent magnet arrangements intersects to define the acute angle.

7. The ultrasonic probe according to claim 3, wherein:
the ultrasonic transducer segments comprise electromagnetic ultrasonic transducers and the test specimen contains at least components of ferromagnetic and/or electrically conductive material.

8. The ultrasonic probe according to claim 7, wherein:
the at least two segment parts each comprise a permanent magnet arrangement including individual bar magnets joined directly to one another in a stack with each bar magnet having magnetic poles alternating in a direction of stacking; and further comprising:
a HF coil containing coils connected in series which are each associated with a different permanent magnet arrangement and a direction of stacking of the permanent magnet arrangements intersects to define the acute angle.

9. The ultrasonic probe according to claim 7, wherein:
pairs of segment parts each include a HF coil arrangement having a plurality of coil loops arranged along the coil arrangement;
bodies of pairs of HF coil arrangements each have an axis which intersects to define the acute angle;
the HF coil arrangements of each segment part are connected; and
a magnet arrangement applies a stationary or quasi-stationary magnetic field oriented parallel to the surface of the test specimen at a location of the HF coil arrangements.

10. The ultrasonic probe according to claim 2, wherein:
the ultrasonic transducer segments comprise a piezoelectric material for transducing sound; and
the at least two segment parts include a transducer body comprising the piezoelectric material, having a longitudinal extension, for application to the test specimen and the longitudinal extension of the transducer bodies intersect to define the acute angle.

11. The ultrasonic probe according to claim 10, wherein:
the ultrasonic transducer segments comprise electromagnetic ultrasonic transducers and the test specimen contains at least components of ferromagnetic and/or electrically conductive material.

12. The ultrasonic probe according to claim 11, wherein:
the at least two segment parts each comprise a permanent magnet arrangement including individual bar magnets joined directly to one another in a stack with each bar magnet having magnetic poles alternating in a direction of stacking; and further comprising:
a HF coil containing coils connected in series which are each associated with a different permanent magnet arrangement and a direction of stacking of the permanent magnet arrangements intersects to define the acute angle.

13. The ultrasonic probe according to claim 11, wherein:
pairs of segment parts each include a HF coil arrangement having a plurality of coil loops arranged along the coil arrangement;
bodies of pairs of HF coil arrangements each have an axis which intersects to define the acute angle;
the HF coil arrangements of each segment part are connected; and a magnet arrangement applies a stationary or quasi-stationary magnetic field oriented parallel to the surface of the test specimen at a location of the HF coil arrangements.

14. The ultrasonic probe according to claim 2, wherein:
the ultrasonic transducer segments comprise electromagnetic ultrasonic transducers and the test specimen contains at least components of ferromagnetic and/or electrically conductive material.

15. The ultrasonic probe according to claim 14, wherein:
the at least two segment parts each comprise a permanent magnet arrangement including individual bar magnets joined directly to one another in a stack with each bar magnet having magnetic poles alternating in a direction of stacking; and further comprising:
a HF coil containing coils connected in series which are each associated with a different permanent magnet arrangement and a direction of stacking of the permanent magnet arrangements intersects to define the acute angle.

16. The ultrasonic probe according to claim 14, wherein:
pairs of segment parts each include a HF coil arrangement having a plurality of coil loops arranged along the coil arrangement;
bodies of pairs of HF coil arrangements each have an axis which intersects to define the acute angle;
the HF coil arrangements of each segment part are connected; and
a magnet arrangement applies a stationary or quasi-stationary magnetic field oriented parallel to the surface of the test specimen at a location of the HF coil arrangements.

17. The ultrasonic probe according to claim 1, wherein:
the ultrasonic transducer segments emit ultrasonic plate waves.

18. The ultrasonic probe according to claim 17, wherein:
the ultrasonic transducer segments comprise a piezoelectric material for transducing sound; and
the at least two segment parts include a transducer body comprising the piezoelectric material, having a longitudinal extension, for application to the test specimen and the longitudinal extension of the transducer intersect to define the acute angle.

19. The ultrasonic probe according to claim 18, wherein:
the ultrasonic transducer segments comprise electromagnetic ultrasonic transducers and the test specimen contains at least components of ferromagnetic and/or electrically conductive material.

20. The ultrasonic probe according to claim 19, wherein:
the at least two segment parts each comprise a permanent magnet arrangement including individual bar magnets joined directly to one another in a stack with each bar magnet having magnetic poles alternating in a direction of stacking; and further comprising:
a HF coil containing coils connected in series which are each associated with a different permanent magnet arrangement and a direction of stacking of the permanent magnet arrangements intersects to define the acute angle.

21. The ultrasonic probe according to claim 19, wherein:
pairs of segment parts each include a HF coil arrangement having a plurality of coil loops arranged along the coil arrangement;
bodies of pairs of HF coil arrangements each have an axis which intersects to define the acute angle;
the HF coil arrangements of each segment part are connected; and
a magnet arrangement applies a stationary or quasi-stationary magnetic field oriented parallel to the surface of the test specimen at a location of the HF coil arrangements.

22. The ultrasonic probe according to claim 17, wherein:
the ultrasonic transducer segments comprise electromagnetic ultrasonic transducers and the test specimen contains at least components of ferromagnetic and/or electrically conductive material.

23. The ultrasonic probe according to claim 22, wherein:
the at least two segment parts each comprise a permanent magnet arrangement including individual bar magnets joined directly to one another in a stack with each bar magnet having magnetic poles alternating in a direction of stacking; and further comprising:
a HF coil containing coils connected in series which are each associated with a different permanent magnet arrangement and a direction of stacking of the permanent magnet arrangements intersects to define the acute angle.

24. The ultrasonic probe according to claim 22, wherein:
pairs of segment parts each include a HF coil arrangement having a plurality of coil loops arranged along the coil arrangement;
bodies of pairs of HF coil arrangements each have an axis which intersects to define the acute angle;
the HF coil arrangements of each segment part are connected; and
a magnet arrangement applies a stationary or quasi-stationary magnetic field oriented parallel to the surface of the test specimen at a location of the HF coil arrangements.

25. The ultrasonic probe according to claim 1, wherein:
the ultrasonic transducer segments comprise a piezoelectric material for transducing sound; and
the at least two segment parts include a transducer body comprising the piezoelectric material, having a longitudinal extension, for application to the test specimen and the longitudinal extension of the transducer bodies intersect to define the acute angle.

26. The ultrasonic probe according to claim 25, wherein:
the ultrasonic transducer segments comprise electromagnetic ultrasonic transducers and the test specimen contains at least components of ferromagnetic and/or electrically conductive material.

27. The ultrasonic probe according to claim 26, wherein:
the at least two segment parts each comprise a permanent magnet arrangement including individual bar magnets joined directly to one another in a stack with each bar magnet having magnetic poles alternating in a direction of stacking; and further comprising:
a HF coil containing coils connected in series which are each associated with a different permanent magnet arrangement and a direction of stacking of the permanent magnet arrangements intersects to define the acute angle.

28. The ultrasonic probe according to claim 26, wherein:
pairs of segment parts each include a HF coil arrangement having a plurality of coil loops arranged along the coil arrangement;
bodies of pairs of HF coil arrangements each have an axis which intersects to define the acute angle;
the HF coil arrangements of each segment part are connected; and
a magnet arrangement applies a stationary or quasi-stationary magnetic field oriented parallel to the surface of the test specimen at a location of the HF coil arrangements.

29. The ultrasonic probe according to claim 1, wherein:

the ultrasonic transducer segments comprise electromagnetic ultrasonic transducers and the test specimen contains at least components of ferromagnetic and/or electrically conductive material.

30. The ultrasonic probe according to claim 29, wherein:

the at least two segment parts each comprise a permanent magnet arrangement including individual bar magnets joined directly to one another in a stack with each bar magnet having magnetic poles alternating in a direction of stacking; and further comprising:

a HF coil containing coils connected in series which are each associated with a different permanent magnet arrangement and a direction of stacking of the permanent magnet arrangements intersects to define the acute angle.

31. The ultrasonic probe according to claim 29, wherein:

pairs of segment parts each include a HF coil arrangement having a plurality of coil loops arranged along the coil arrangement extending in a direction;

bodies of pairs of HF coil arrangements each have an axis which intersects to define the acute angle;

the HF coil arrangements of each segment part are connected; and a magnet arrangement applies a stationary or quasi-stationary magnetic field oriented parallel to the surface of the test specimen at a location of the HF coil arrangements.

32. The ultrasonic probe according to claim 31, wherein:

the permanent magnetic arrangements are disposed relative to HF coil arrangements to define an angle $\beta$ between a direction of a magnetic field of the permanent magnetic arrangements and directions of an axis of the HF coil arrangements equals:

a) $\beta=90°\pm$ the acute angle divided by two or b) $\beta=\pm$ the acute angle divided by two.

33. The ultrasonic probe according to claim 1, wherein:

the acute angle ranges from $0°<$ the acute angle $<90°$.

34. A method for the nondestructive testing of a test specimen with ultrasonic plate waves generated by a plurality of ultrasonic transducer segments, the plurality of ultrasonic transducer segments being activated individually or in groups as a phased array for emission of ultrasonic plate waves in a predefinable propagation direction into the test specimen comprising activating at least one ultrasonic transducer segment to emit at least two overlapping ultrasonic plate wave fields which are spatially superpositioned at the same time intersecting in an acute angle.

35. An ultrasonic probe for nondestructive testing of a test specimen, comprising:

a plurality of ultrasonic transducer segments which are activatable individually or in groups as a phased array to emit and to receive reflected ultrasonic plate waves having a predefinable propagation direction in the test specimen to be tested; and wherein:

at least one ultrasonic transducer segment includes at least two segment parts, each for emitting an ultrasonic plate wave field into the test specimen and for receiving a reflection of the ultrasonic plate wave fields and which are activatable jointly and simultaneously as a phased array and the at least two segment parts are disposed along a common plane so that the ultrasonic wave fields emitted from the at least two segments and received by the at least two segments mutually overlap and each have a main propagation direction intersecting in an acute angle defined in a plane.

36. A method for the nondestructive testing of a test specimen with ultrasonic plate waves generated by a plurality of ultrasonic transducer segments and received by the plurality of ultrasonic transducer segments, the plurality of ultrasonic transducer segments being activated individually or in groups as a phased array for emission of ultrasonic plate waves further in a predefinable propagation direction into the test specimen and for receiving ultrasonic plate wave fields at a predefined propagation direction reflected from the test specimen comprising activating at least one ultrasonic transducer segment to emit and to receive at least two overlapping ultrasonic plate wave fields which are spatially superpositioned at the same time and intersect in a plane in an acute angle.

* * * * *